(12) United States Patent
Picanco et al.

(10) Patent No.: US 8,759,254 B2
(45) Date of Patent: Jun. 24, 2014

(54) FERTILIZER—PESTICIDE THROW-PACK

(75) Inventors: Rui Luiz Correa Picanco, Cary, NC (US); Guillaume Huchet, Lawrence, KS (US); Charles William Boyd, Wake Forest, NC (US); Stephanie Darnell, Raleigh, NC (US); Kenneth James Essig, Wake Forest, NC (US); Raymond L. Cheek, Holt, MO (US)

(73) Assignee: Bayer Cropscience LP, Research Triangle Park, NC (US)

( * ) Notice: Subject to any disclaimer, the term of this patent is extended or adjusted under 35 U.S.C. 154(b) by 0 days.

(21) Appl. No.: 12/921,455

(22) PCT Filed: May 5, 2009

(86) PCT No.: PCT/US2009/042775
§ 371 (c)(1),
(2), (4) Date: Dec. 9, 2010

(87) PCT Pub. No.: WO2009/137434
PCT Pub. Date: Nov. 12, 2009

(65) Prior Publication Data
US 2011/0071025 A1    Mar. 24, 2011

Related U.S. Application Data

(63) Continuation of application No. 12/151,704, filed on May 8, 2008, now abandoned.

(51) Int. Cl.
| | | |
|---|---|---|
| *A01N 25/34* | (2006.01) | |
| *A01N 43/40* | (2006.01) | |
| *A01N 43/54* | (2006.01) | |
| *C07D 213/26* | (2006.01) | |
| *C07D 401/06* | (2006.01) | |
| *B65D 37/00* | (2006.01) | |

(52) U.S. Cl.
USPC ........ 504/113; 504/116.1; 504/118; 504/187; 504/188; 504/358; 504/360; 504/361; 47/65; 47/65.5; 47/65.8; 47/66.7; 47/74; 546/1; 546/268.1; 546/274.7; 546/275.1; 206/205; 206/591

(58) Field of Classification Search
USPC ............. 504/113, 116.1, 118, 187, 188, 358, 504/360, 361; 47/65, 65.5, 65.8, 66.7, 74; 546/1, 268.1, 274.7, 275.1; 206/205, 206/591
See application file for complete search history.

(56) References Cited

U.S. PATENT DOCUMENTS

| | | | | |
|---|---|---|---|---|
| 4,315,763 | A * | 2/1982 | Stoller et al. | 71/29 |
| 4,627,191 | A * | 12/1986 | Bergere | 47/32 |
| 4,983,390 | A * | 1/1991 | Levy | 424/404 |
| 5,317,834 | A * | 6/1994 | Anderson | 47/48.5 |
| 5,335,449 | A * | 8/1994 | Beatty | 47/48.5 |
| 5,346,068 | A * | 9/1994 | Gouge et al. | 206/524.7 |
| 7,087,239 | B2 | 8/2006 | Bratz et al. | |
| 2002/0026747 | A1* | 3/2002 | Howe et al. | 47/48.5 |
| 2006/0063674 | A1 | 3/2006 | Morris et al. | |
| 2007/0167327 | A1* | 7/2007 | Savich et al. | 504/101 |
| 2008/0090728 | A1* | 4/2008 | Rodekohr et al. | 504/101 |

FOREIGN PATENT DOCUMENTS

| | | | | |
|---|---|---|---|---|
| WO | WO97/33463 | * | 9/1997 | A01G 9/02 |
| WO | 2005/112624 | | 12/2005 | |

OTHER PUBLICATIONS

"Polyvinyl Alcohol", Wikipedia [online], retrieved Dec. 18, 2012] Retrieved from the Internet<URL: http://en.wikipedia.org/wiki/PVOH>.*
International Search Report and written opinion for PCT/US09/42775 filed May 5, 2009.
European Search Report based on Application No. 09743420.3-2103/2285758 PCT/US2009042775 mailed Dec. 3, 2012.

* cited by examiner

*Primary Examiner* — Jane C Oswecki
(74) *Attorney, Agent, or Firm* — Miles & Stockbridge, P.C.

(57) ABSTRACT

The present invention relates to a product for use with new plants comprising a package which is optionally degradable, wherein said package forms an enclosed space is provided. At least one plant enhancer at least one pesticide, and/or at least one pesticide is located in the enclosed space formed by the package. The invention further is directed to method for treating a plant and to method for reducing shock to a plant.

11 Claims, No Drawings

FERTILIZER—PESTICIDE THROW-PACK

BACKGROUND OF THE INVENTION

1. Field of the Invention

The invention relates to a product comprising plant enhancers, pesticide, and water absorbing material contained within a package, which is optionally degradable. In particular, the invention relates to a product suitable for use, for example, when planting new trees, flowers, and shrubs, comprising a pesticide, plant enhancers, and water absorbing material contained within a degradable package that controls insects, promotes plant growth, and reduces the need for plant watering, thus, enhancing plant stress tolerance.

2. Background of the Invention

Fertilizers and pesticides are important compounds for providing newly planted trees and shrubs a healthy start. Specifically, plant enhancers and pesticides protect against damaging insects, promote growth, reduce stress, and provide the necessary nutrition. When planting trees and shrubs, a novice gardener usually places the plant into a pre-dug hole, fills in the gaps with soil, and adds water. Absent an occasional watering, the novice ceases to care for the new plant. A veteran may follow the above, but will add a handful of plant enhancers in either dry or wet form after planting, and frequently water. The control of insects usually takes place much later, after the gardener observes visible insect damage to the leaves. Regardless of how careful the gardener is in planting, the plant will suffer from "transplant shock" as it goes from container to hole. Transplant shock is caused by the sudden change in environment, and disruption in nutrient and water supply. Transplant shock is a major contributor to death in newly planted plants.

Degradable packages can be water soluble or degradable packages, among many other possibilities. The water soluble packages are typically made from either polyvinyl alcohol ("PVA") or biodegradable paper. U.S. Pat. No. 3,892,905 discloses a cold water soluble PVA package containing a pesticide for use in liquid application of the pesticide. Here, the consumer would place the package into a known quantity of water, thereby diluting the pesticide to the correct concentration. Similarly, U.S. Pat. No. 4,156,047 discloses a melt processable PVA film for forming packages. U.S. Pat. No. 4,544,693 discloses a PVA film comprising a polymer blend that results in a humidity tolerant package for holding agrochemicals. Similarly, U.S. Pat. No. 4,692,494 discloses a humidity tolerant film comprising PVA and polyacrylic acid. U.S. Pat. No. 5,272,191 discloses a PVA film comprising a water insoluble cellulose material that aids in dissolving the PVA film. U.S. Pat. No. 6,783,006 discloses a two-layer soluble package for holding water dispersible powders or granulates. None of these patents disclose placing the package into a planting hole prior to inserting a plant.

SUMMARY OF THE INVENTION

The present invention provides a combination plant enhancer—pesticide product suitable for use when planting new trees, flowers, and shrubs, to reduce transplant shock. Specifically, a product of the present invention comprises a package comprising at least one the following: a plant enhancer, a pesticide, and a water absorbent material wherein the package is capable of being placed into a planting hole after insertion of a plant. The package provides an easy one-step procedure for a consumer to get their plants off to a good start. Adding the correct and/or ideal amounts of individual ingredients separately into the planting hole is difficult, time consuming, and unlikely to be done by a novice or even a veteran gardener. Further, application of incorrect amounts could shock or starve the plant, thereby increasing transplant shock, plant disease or even plant death. Also, placing the package close to the roots results in less water run off and UV degradation over applying individual ingredients on top of the soil. A package of the present invention provides a pre-measured combination that protects the plant from damage by insects, promotes plant growth, and reduces plant watering necessity, thus enhancing plant stress tolerance. The increased plant stress tolerance decreases the chances of plant death due to transplant shock, especially with the novice gardener, and increase plant vitality, thereby resulting in a healthier plant and happier gardener. Further, products as well as methods of the present invention may also provide one or more further benefits such as increase plant growth, provide slow release feeding, increase plant survival, improve water retention, reduce watering frequency and necessity, reduce plant and root heat stress, promote rapid root growth, improve soil aeration and the like. Moreover, a package of the present invention provides easy storage and takes up less shelf space, since multiple single ingredients do not need to be stored.

According to one aspect of the invention, a product is provided that is suitable for application into a planting hole after insertion of a plant. Here, the product comprises a package, wherein said package forms an enclosed space and is optionally degradable; and at least one component selected from the group consisting of a plant enhancer, a pesticide; and a water absorbing material, wherein said at least one component is located in said enclosed space of said package.

In another aspect of the invention, a method of treating a plant is provided, comprising placing a plant into a hole; placing at least one package comprising at least one plant enhancer, at least one pesticide, and/or at least one water absorbent material into said hole; and watering said plant, wherein said plant enhancer, pesticide, and/or water absorbent material are dispersed throughout said hole.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out in the appended claims.

DETAILED DESCRIPTION OF THE INVENTION

The present invention relates to a novel product for the reduction of transplant shock in new plants.

Generally, the invention comprises a package comprising at least one of the following: a plant enhancer, a pesticide, and a water absorbent material for placement into a planting hole after inserting the plant. Plant enhancers are generally intended for the improvement, maintenance, survival, health and propagation of plants and can comprise, for example, a plant nutrient, a trace element, a nutritional chemical, a plant inoculant, a soil amendment, a vitamin hormone horticultural product or the like. In one embodiment, the at least one plant enhancer and pesticide are pre-measured to provide the correct amount for approximately a single plant specimen. Packages can also be combined, if desired, for larger plants. For example, a new tree with about a ¾ inch trunk diameter typically requires two packages. The water absorbent material aids in retaining water near the plant roots by absorbing water from nearby soil. This water retention characteristic doubles the permanent wilting point of most plants under normal growing conditions. Further, the water absorbent material, in combination with the package degradation, disperses the plant enhancers and pesticide within the plant hole. A package of the present invention in one embodiment can be something like a teabag in that it can comprise components inside a porous outer shell whereby the components inside the package can leech out of the shell and then be absorbed into the soil or plant that is adjacent thereto. The package can be fibrous material, for example, that does not degrade, but does not harm the soil. In another embodiment, the package can be degradable or even biodegradable. Alternatively, in another embodiment, the package can be opened by a user just before application and the components within the package can be added to the soil, to seeds, to a plant or to a fruit or an area adjacent thereto.

In a preferred embodiment, the plant enhancer can be a fertilizer. The fertilizer can comprise any combination of dry nutrients, such as for example nitrogen, potassium, phosphorous, soda ash, and magnesium. Preferably, the fertilizer is a combination of nitrogen, potassium, and phosphorous and other micro-nutrients. Most preferably, the fertilizer is a combination of nitrogen, potassium, and phosphorous in a ratio of approximately 1:2:1.

The pesticide can be any compound known to a person of skill in the art that is capable of controlling pest populations on or around plants such as through root uptake of the pesticide. Pesticides include any substance or mixture of substances used for preventing, controlling, or lessening the damage caused by a pest. A pesticide may be a chemical substance, biological agent such as a virus or bacteria, antimicrobial, or a disinfectant. Pests include for example, insects, plant pathogens, weeds, mollusks, birds, mammals, fish, nematodes such as roundworms, microbes as well anything that causes or could cause damage to a growing plant, seed or fruit.

Suitable pesticides include insecticides which are a specific category of pesticides for the control of insects, namely ovicides (substances that kill eggs), larvicides (substances that kill larvae), or adulticides (substances that kill adult insects). Pesticides can also include miticides, acaricides, mulluscides, nematicides, and other varieties of agents. Preferably, the pesticide is a chloronicotinyl. Most preferably, the pesticide is imidacloprid.

The water absorbent material can be any compound known to a person of skill in the art that is capable of uptaking and storing water. Preferably, the water absorbent material is a cellulose or a polymeric material and in one embodiment the water absorbent material comprises a potassium acrylate copolymer. Most preferably, the water absorbent material is Stockosorb™ available from Degussa Stockhausen, Inc.

Preferably the package is a degradable package. The degradable package can be, for example any container known to a person of skill in the art to dissolve either in the presence of water or other substances. If the package is not degradable and if the entire package is intended to be buried into the soil as a single unit with its contents, the outer package is of a composition that will allow components therein to leech out over time. If the package is to be opened prior to being applied to the soil or plant, the outer package can be any desired material that can hold the components and preferably keep them shelf stable over temperatures from 0-50 degrees Celcius and at a wide range of humidity levels.

Biodegradable packages are advantageous in some embodiments. Examples of suitable packages include polyvinyl alcohol films, thermoplastic polyvinyl alcohol, biodegradable paper, biodegradable polymer, and/or biodegradable cloth. In one embodiment, the degradable package will dissolve in the presence of water at a temperature which is from about 4° C. to about 40° C. Preferably, the degradable package comprises polyvinyl alcohol. Most preferably, the package is a polyvinyl alcohol supplied by MonoSol, LLC. The degradable package can advantageously be any two dimensional shape that is designed to hold dry ingredients when in three dimensional form. Such two dimensional shapes include, but are not limited to, squares, ovals, triangles, stars, circles, rectangles, pentagons, hexagons, and octagons. Preferably, the shape is rectangular. The degradable package can also be any size. Preferably, the size will result in an interior volume of about 0.1 ounces to about 8 ounces, and most preferably about 1.3 ounces.

In another embodiment, the pesticide is attached to a plant enhancer to form a unitary compound. U.S. Pat. No. 5,783,203, herein incorporated by reference in its entirety, discloses a process for making an integrated insecticide/fertilizer compound. In such a case of a unitary compound, the fertilizer and pesticide may be mixed with water, solid carrier particles, binders, and/or other additives to form an integrated fertilizer/pesticide compound. The fertilizer can comprise any combination of nutrients, such as, nitrogen, potassium, phosphorous, soda ash, and magnesium. Preferably, the fertilizer is a combination of nitrogen, potassium, and phosphorous. Most preferable, the fertilizer is a combination of nitrogen, potassium, and phosphorous in a ratio of approximately 1:2:1. The pesticide can be any compound known to a person of skill in the art that controls pest population on or around plants. Preferably, the pesticide is a chloronicotinyl. Most preferably, the pesticide is imidacloprid.

The weight percent of each component in a single package can vary depending on the size of the plant to be treated. The package can contain at least one of the components, namely the pesticide, the plant enhancer and the water absorbing material. In one advantageous embodiment all three components are present in the package. Generally, the weight percent of the pesticide is about 0.001% to about 99.9% by weight, and preferably about 0.2-2.5%, more preferably from 0.5-1.5%, and in one specific embodiment about 0.69% by weight. The weight percent of plant enhancers varies from about 0.001% to about 99.9% by weight, preferably from 20-99%, more preferably from 50-90% or from 60-85%, and in one specific embodiment, about 79% by weight. The weight percent of the water absorbing material is from about 0.001% to about 99.9%, and preferably from 2-40%, more preferably from 15-35%, and in one specific embodiment, about 20%. The overall weight of the components in a single package is generally between about 0.1 ounces to about 8.0 ounces, and preferably about 1.3 ounces.

A single degradable package can treat a single newly planted shrub, while two packages may be needed for newly planted trees. The quantities needed for various applications can be adapted as desired and based on the intended uses. Larger packages can be used if the intention is to utilize for large shrubs or trees, while smaller packages can be utilized to insert into burrows for annual flowers, or in gardens, for example. To use the degradable package, generally the consumer would dig a hole slightly larger than the container holding the plant. Place the plant's soil/root network inside the hole. Place the correct number of packages about 4 inches to 6 inches deep between the sides of the hole and the sides of the plant's soil/root network. Fill in the hole with soil and water. Each application provides up to about three months of nutrients, moisture control, and insect protection. If the package is not to be buried in the soil, the user can just open the package and apply the contents to the hole where the tree or plant will be planted.

A package of the present invention can be used to control a variety of insects, such as adelgids, aphids, lace bugs, leafminers, scale, whiteflies, fungus gnats, Japanese beetles, leaf beetles, leafhoppers, mealybugs, pine tip moth larvae, psyllids, root weevil larvae, royal palm bugs, sawfly larvae, thrips, white grub larvae, and other pests.

In a further embodiment, the soluble package may be used in transporting a plant from the ground to a container for transport to a different location or storage. Here, the plant's soil/root network is placed inside the container and the soluble package placed between the soil/root network and the container side. Soil is added to fill the gap between the container and soil/root network. Water is added until the container is saturated. The use of the degradable package in this situation lowers transplant shock and extends the plant's storage life while in the container.

A product suitable for use when planting a plant comprising: a package, wherein said package forms an enclosed space and is optionally degradable; and at least one component selected from the group consisting of a plant enhancer, a pesticide; and a water absorbing material, wherein said at least one component is located in said enclosed space of said package, and wherein said pesticide is present in about 0.50% to about 0.90% by weight of total contents in said package with a 75% nominal pesticide concentration, said plant enhancer is present in about 70% to about 85% by weight of total contents in said package, and said water absorbing material is present in about 15% to about 30% by weight of total contents in said package.

The product of the disclosure above wherein said plant enhancer comprises a fertilizer.

The product of the disclosure above wherein said plant enhancer comprises nitrogen, potassium and/or phosphorus.

The product of the disclosure above wherein said nitrogen, potassium and phosphorus are present in a ratio of about 12:1.

The product of the disclosure above wherein said pesticide is a chloronicotinyl.

The product of the disclosure above wherein said pesticide is imidacloprid.

The product of the disclosure wherein said pesticide and said plant enhancer comprises a granule combination comprising said pesticide adhered to said plant enhancer.

The product of the disclosure above wherein said water absorbent material is a cellulose or a polymer.

The product of the disclosure above wherein said water absorbing material is an acrylate polymer.

The product of the disclosure above wherein said pesticide is present in an amount of about 0.69% by weight of total contents in said package with a 75% nominal pesticide concentration, said plant enhancer is present in an amount of about 78.9% by weight of total contents of said package, and said water absorbing material is present in an amount of about 19.7% by weight of the total contents in said package.

The product of the disclosure above wherein said package is biodegradable.

A method of treating a plant comprising: placing a plant into a hole; placing at least one package comprising at least one plant enhancer, at least one pesticide, and/or at least one water absorbent material into said hole; and watering said plant, wherein said plant enhancer, pesticide, and/or water absorbent material are dispersed throughout said hole, and wherein said pesticide is present in about 0.50% to about 0.90% by weight of total contents in said package with a 75% nominal pesticide concentration, said plant enhancer is present in about 70% to about 85% by weight of total contents in said package, and said water absorbing material is present in about 15% to about 30% by weight of total contents in said package.

The method of the disclosure above wherein said pesticide is a chloronicotinyl.

The method of the disclosure above wherein said pesticide is imidacloprid.

The method of the disclosure above wherein said plant enhancer comprises nitrogen, potassium and phosphorus.

The method of the disclosure above wherein said water absorbing material is a cellulose or a polymer.

The method of the disclosure above wherein said water absorbing material is an acrylate polymer.

The method of the disclosure above wherein said package is degradable.

The method of the disclosure above wherein said method reduces transplant shock in a newly planted plant.

EXAMPLES

Example 1

Example 1 shows the results of the degradable package on Cherry tree growth. The package contained the following components: 75 WP imidacloprid insecticide at a concentration of 0.92% by weight of total components; mineral oil at a concentration of 0.5% by weight of total components; Stockosorb™ at a concentration of 19.7% by weight of total components; and fertilizer 6-10-6 at a concentration of 78.88% by weight of total components. The control contained no plant enhancers or pesticides. The study was conducted in White Heath, Ill. over a three month period. A total of eight trees were studied, four with no treatment and four treated with the degradable package at the time of planting. The soil/root network of each tree was placed inside a hole slightly larger than the network. Two degradable packages were placed into each of the holes between the soil/root network and the hole sides at opposite ends, and at about 4 to 6 inches below the surface. Soil was filled around the soil/root network and the area surrounding the trees saturated with water. About 2-4 inches of mulch was placed around the trunk of each tree. After three months, the average diameter of the Cherry trees treated with the degradable package was twice as much as the average diameter of the untreated Cherry trees.

| Treatment | Average Girth in inches after 3 Months |
|---|---|
| Control | 0.75 |
| Degradable Package | 1.5 |

Example 2

Example 2 shows the results of the degradable package on rose bush growth. The package contained the following components: 75 WP imidacloprid insecticide at a concentration of 0.92% by weight of total components; mineral oil at a concentration of 0.5% by weight of total components; Stockosorb™ at a concentration of 19.7% by weight of total components; and fertilizer 6-10-6 at a concentration of 78.88% by weight of total components. The control contained no plant enhancers or pesticides. The study was conducted in White Heath, Ill. over a three month period. A total of eight bushes were studied, four with no treatment and four treated with the degradable package at the time of planting. The soil/root network of each bush was placed inside a hole slightly larger than the network. One degradable package was placed into each of the holes between the soil/root network and the hole sides, and at about 4 to 6 inches below the surface. Soil was filled around the soil/root network and the area surrounding the bushes saturated with water. About 2-4 inches of mulch was placed around each bush. After three months, the average height of the rose bushes treated with the degradable package was about the same as the average diameter of the untreated rose bushes.

| Treatment | Average Height in Feet after 3 Months |
| --- | --- |
| Control | 1.37 |
| Degradable Package | 1.3 |

Example 3

Example 3 shows the results of the degradable package on rose bush flower growth. The package contained the following components: 75 WP imidacloprid insecticide at a concentration of 0.92% by weight of total components; mineral oil at a concentration of 0.5% by weight of total components; Stockosorb™ at a concentration of 19.7% by weight of total components; and fertilizer 6-10-6 at a concentration of 78.88% by weight of total components. The control contained no plant enhancers or pesticides. The studies were conducted at White Heath, Ill. and Clayton, N.C. A total of sixteen bushes were studied (eight at each location), eight with no treatment and eight treated with the degradable package. The soil/root network of each bush was placed inside a hole slightly larger than the network. One degradable package was placed into each of the holes between the soil/root network, and at about 4 to 6 inches below the surface. Soil was filled around the soil/root network and the area surrounding the bushes saturated with water. About 2-4 inches of mulch was placed around each bush. After three months, the average number of flowers on rose bushes treated with the degradable package was about 16% more than the average number of flowers on untreated rose bushes.

| Treatment | Average Number of Flowers after 3 Months |
| --- | --- |
| Control | 4.4 |
| Degradable Package | 5.25 |

Example 4

Example 4 shows the average vigor ratings (1=dead or poor plant; 10=excellent plant) on Oleander and *Eugenia Myrtifolia* plant species treated with the degradable package. The package contained the following components: 75 WP imidacloprid insecticide at a concentration of 0.92% by weight of total components; mineral oil at a concentration of 0.5% by weight of total components; Stockosorb™ at a concentration of 19.7% by weight of total components; and fertilizer 6-10-6 at a concentration of 78.88% by weight of total components. The control contained no plant enhancers or pesticides. The studies were conducted at Valley Center, California. A total of sixteen plants were studied (eight of each plant species), four with no treatment and four treated with the degradable pack-age. The soil/root network of each plant was placed inside a container slightly larger than the original network. One degradable package was placed between the soil/root network and the container. Soil was filled around the soil/root network and the area surrounding the plants saturated with water. After 91 days, the Oleander plants showed about a 7% average increase in vigor over the untreated plants, and the *Eugenia Myrtifolia* plants showed about an 8% average increase in plant vigor over the untreated plants.

| Treatment | Vigor Ratings on *Oleander* after 91 days | Vigor Ratings on *Eugenia Myrtifolia* after 91 days |
| --- | --- | --- |
| Control | 7.9 | 6.8 |
| Degradable Package | 8.5 | 7.4 |

Example 5

Example 5 shows the average plant heights in inches of Oleander, *Eugenia Myrtifolia* and *Photinia fraserii* 189 days after being treated with the degradable package. The package contained the following components: 75 WP imidacloprid insecticide at a concentration of 0.92% by weight of total components; mineral oil at a concentration of 0.5% by weight of total components; Stockosorb™ at a concentration of 19.7% by weight of total components; and fertilizer 6-10-6 at a concentration of 78.88% by weight of total components. The control contained no plant enhancers or pesticides. The studies were conducted at Valley Center, California. A total of twenty four plants were studied (eight of each plant species), four with no treatment and four treated with the degradable package. The soil/root network of each plant was placed inside a container slightly larger than the root original network. One degradable package was placed between the soil/root network and the containers. Soil was filled around the soil/root network and the area surrounding the plants saturated with water. After 189 days, the Oleander plants showed about a 14% average increase in plant height over the untreated plants, the *Eugenia Myrtifolia* plants showed about a 4% average increase in plant height over the untreated plants, and the *Photinia fraserii* showed about a 12% average increase in plant height over the untreated plants.

| Treatment | *Oleander* Plant Height (in) after 189 Days | *Eugenia Myrtifolia* Plant Height (in) after 189 Days | *Photinia fraserii* Plant Height (in) after 189 Days |
| --- | --- | --- | --- |
| Control | 28.3 | 54.0 | 22.1 |
| Degradable Package | 32.8 | 56.2 | 25.2 |

The results above are surprising. A person of skill in the art would expect that these results were from applying the package components individually, over the entire plant area. This expectation stems from, among other things, the degradable packaged not dispersing the components in a manner that results in increased plant size. One might expect the package contents to remain in a fixed location, possibly destroying the plant roots because of a high concentration of fertilizer in a localized area. Root damage caused by high concentrations of fertilizer would result in stunted plant grown. As shown above, however, this is not the case.

Further, the above results show that regardless of where the package is used, increase plant size results. The results were conducted at three separate locations: North Carolina, Illinois, and California. Each location has a soil composition distinct from the others. In one location, the soil may not be lacking in nutrients. In another location, the soil may not be subject to drought conditions. In another, there is no insect problem. A person of skill in the art would expect that only one or two of the package ingredients is needed, and therefore, would not combine all three. For example, combining all three in a location with rich soil and none drought conditions may result in decreased plant size because of the presence of too much plant nutrients and water. As shown above, however, the package results in increased plant size regardless of the soil conditions. This is unexpected.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All documents referred to herein are specifically incorporated herein by reference in their entireties.

As used herein and in the following claims, articles such as "the", "a" and "an" can connote the singular or plural.

What we claim is:

1. A product suitable for use when planting a plant comprising:
    (a) a package comprising polyvinyl alcohol, wherein said package will dissolve in the presence of water and forms an enclosed space; and
    (b) a plant enhancer comprising fertilizer, a pesticide comprising imidacloprid, and a potassium acrylate copolymer, located in said enclosed space of said package,
    wherein said pesticide is present in an amount of about 0.50% to about 0.90% by weight of total contents in said package, said plant enhancer is present in an amount of about 70% to about 85% by weight of total contents in said package, and said potassium acrylate copolymer is present in an amount of about 15% to about 30% by weight of total contents in said package, wherein said pesticide, plant enhancer, and potassium acrylate copolymer do not exceed 100% by weight of the total contents in said package.

2. The product of claim 1, further comprising at least one root stimulant.

3. The product of claim 1, wherein the plant enhancer of component (b) comprises nitrogen, potassium, and phosphorus.

4. The product of claim 3, wherein said nitrogen, potassium, and phosphorus are present in a ratio of about 1-2-1.

5. The product of claim 1, wherein the pesticide and plant enhancer of component (b) together comprise a granule combination comprising said pesticide adhered to said plant enhancer.

6. The product of claim 1, wherein said pesticide is present in an amount of about 0.69% by weight of total contents in said package with a 75% nominal pesticide concentration, said plant enhancer is present in an amount of about 78.9% by weight of total contents in said package, and said potassium acrylate copolymer is present in amount of about 19.7% by weight of total contents in said package.

7. A method of treating a plant comprising:
    (a) placing a plant into a hole;
        (b) placing into said hole, at least one water dissolvable package comprising polyvinyl alcohol, wherein said package forms an enclosed space and comprises within said enclosed space at least one plant enhancer comprising fertilizer, at least one pesticide comprising imidacloprid, and at least one potassium acrylate copolymer; and
    (c) watering said plant, wherein said plant enhancer, pesticide, and water absorbent material are dispersed throughout said hole,
    wherein said pesticide is present in an amount of from 0.50% to 1.50% by weight of total contents in said package with a 75% nominal pesticide concentration, said plant enhancer is present in an amount of from 50% to 90% by weight of total contents in said package, and said potassium acrylate copolymer is present in an amount of from 15% to 35% by weight of total contents in said package, wherein said pesticide, plant enhancer, and potassium acrylate copolymer do not exceed 100% by weight of the total contents in said package.

8. The method of claim 7, wherein the plant enhancer of component (b) comprises nitrogen, potassium, and phosphorus.

9. The method of claim 7 wherein said method reduces transplant shock in a newly planted plant.

10. The product of claim 1, wherein the plant enhancer of component (b) comprises nitrogen, potassium, or phosphorus.

11. The product of claim 1, wherein the pesticide and plant enhancer of component (b) together comprise a powder.

* * * * *